(12) United States Patent
Kump

(10) Patent No.: US 7,046,764 B1
(45) Date of Patent: May 16, 2006

(54) X-RAY DETECTOR HAVING AN ACCELEROMETER

(75) Inventor: Kenneth S. Kump, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/711,762

(22) Filed: Oct. 4, 2004

(51) Int. Cl.
H05G 1/54 (2006.01)

(52) U.S. Cl. ..................... 378/117; 378/98.8
(58) Field of Classification Search ................ 378/91, 378/98.8, 116–117; 250/207.09, 370.09
See application file for complete search history.

(56) References Cited

U.S. PATENT DOCUMENTS

| | | | |
|---|---|---|---|
| 5,103,092 A | 4/1992 | Takahashi et al. |
| 5,262,871 A | 11/1993 | Wilder et al. |
| 5,281,803 A | 1/1994 | Ishizuka |
| 5,508,740 A | 4/1996 | Miyaguchi et al. |
| 5,514,873 A | 5/1996 | Schulze-Ganzlin et al. |
| 5,608,774 A | 3/1997 | Polichar et al. |
| 5,661,309 A | 8/1997 | Jeromin et al. |
| 5,693,948 A | 12/1997 | Sayed et al. |
| 5,715,292 A | 2/1998 | Sayag et al. |
| 5,773,832 A | 6/1998 | Sayed et al. |
| 5,811,790 A | 9/1998 | Endo et al. |
| 5,828,726 A | 10/1998 | Polichar et al. |
| 5,903,052 A | 5/1999 | Chen et al. |
| 5,909,478 A | 6/1999 | Polichar et al. |
| 5,962,856 A | 10/1999 | Zhao et al. |
| 5,965,872 A | 10/1999 | Endo et al. |
| 6,049,074 A | 4/2000 | Endo et al. |
| 6,127,714 A | 10/2000 | Mochizuki |
| 6,208,708 B1 | 3/2001 | Hoheisel et al. |
| 6,232,607 B1 | 5/2001 | Huang |
| 6,239,439 B1 | 5/2001 | Itabashi et al. |
| 6,255,638 B1 | 7/2001 | Eräluoto et al. |
| 6,323,891 B1 | 11/2001 | Kitani et al. |
| 6,331,705 B1 | 12/2001 | Eisen et al. |
| 6,333,963 B1 | 12/2001 | Kaifu et al. |
| 6,344,652 B1 | 2/2002 | Shoji |
| 6,398,409 B1 | 6/2002 | Brooks |
| 6,459,132 B1 | 10/2002 | Mochizuki |
| 6,469,312 B1 | 10/2002 | Agano |
| 6,475,824 B1 | 11/2002 | Kim |
| 6,552,319 B1 | 4/2003 | Pyyhtiä et al. |
| 6,667,480 B1 | 12/2003 | Kajiwara et al. |
| 6,700,126 B1 | 3/2004 | Watanabe |

(Continued)

FOREIGN PATENT DOCUMENTS

JP 11271454 10/1999

(Continued)

Primary Examiner—David V. Bruce
Assistant Examiner—Hoon Song
(74) Attorney, Agent, or Firm—Ziolkowski Patent Solutions Group, SC; Michael A. Della Penna; Carl B. Horton

(57) ABSTRACT

A method and system of electronically detecting and measuring gravitational loads placed on an x-ray detector is disclosed. An x-ray detector incorporates an accelerometer that detects and provides an output as to the extent of gravitational loads or forces placed thereon. The accelerometer may also time and/or date stamp each recorded event such that a technician may determine when the x-ray detector was subjected to a particular load. A microcontroller/microprocessor may also compare a current reading of the accelerometer to a threshold and, based on the comparison, provide an audio or visual indication that the x-ray detector has been subjected to a potentially damaging gravitational load.

19 Claims, 7 Drawing Sheets

U.S. PATENT DOCUMENTS

| | | |
|---|---|---|
| 6,707,880 B1 | 3/2004 | Yamayoshi |
| 6,714,623 B1 | 3/2004 | Sako et al. |
| 6,723,592 B1 | 4/2004 | Shih |
| 2002/0005490 A1 | 1/2002 | Watanabe |
| 2002/0150214 A1 | 10/2002 | Spahn |
| 2002/0181659 A1 | 12/2002 | Watanabe et al. |
| 2003/0031296 A1* | 2/2003 | Hoheisel .................. 378/98.8 |
| 2003/0136844 A1* | 7/2003 | Dvorkis ................ 235/472.01 |
| 2004/0114725 A1* | 6/2004 | Yamamoto ................. 378/189 |

FOREIGN PATENT DOCUMENTS

| | | |
|---|---|---|
| JP | 2001099942 | 4/2001 |
| JP | 2001198116 | 7/2001 |
| JP | 2001224579 | 8/2001 |
| JP | 2002006049 | 1/2002 |
| JP | 2002014170 | 1/2002 |
| JP | 2002048873 | 2/2002 |
| JP | 2002125960 | 5/2002 |
| JP | 2002131437 | 5/2002 |
| JP | 2003000586 | 1/2003 |
| JP | 2003010175 | 1/2003 |
| JP | 2003014862 | 1/2003 |
| JP | 2003060181 | 2/2003 |
| JP | 2003334184 | 11/2003 |

* cited by examiner

X-RAY DETECTOR HAVING AN ACCELEROMETER

BACKGROUND OF THE INVENTION

The present invention relates generally to x-ray detectors and, more particularly, to a method and system of detecting, measuring, and providing feedback as to gravitational loads placed on an x-ray detector.

X-ray imaging is a non-invasive technique to capture images of medical patients for clinical diagnosis as well as inspect the contents of sealed containers, such as luggage, packages, and other parcels. To capture these images, an x-ray source irradiates a scan subject with a fan beam of x-rays. The x-rays are then attenuated as they pass through the scan subject. The degree of attenuation varies across the scan subject as a result of variances in the internal composition of the subject. The attenuated energy impinges upon an x-ray detector designed to convert the attenuating energy to a form usable in image reconstruction. A control system reads out electrical charge stored in the x-ray detector and generates a corresponding image. For a conventional, screen film detector, the image is developed on a film and displayed using a backlight.

Increasingly, flat panel, digital x-ray detectors are being used to acquire data for image reconstruction. Flat panel detectors are generally constructed as having a scintillator which is used to convert x-rays to visible light that can be detected by a photosensitive layer. The photosensitive layer includes an array of photosensitive or detector elements that each store electrical charge in proportion to the light that is individually detected. Generally, each detector element has a light sensitive region and a region comprised of electronics to control the storage and output of electrical charge. The light sensitive region is typically composed of a photoconductor, and electrons are released in the photoconductor when exposed to visible light. During this exposure, charge is collected in each detector element and is stored in a capacitive element (diode) situated in the electronics region. After exposure, the charge in each detector element is read out using logic controlled electronics.

Each detector element is conventionally controlled using a transistor-based switch. In this regard, the source of the transistor is connected to the diode, the drain of the transistor is connected to a readout line, and the gate of the transistor is connected to a scan control interface disposed on the electronics in the detector. When negative voltage is applied to the gate, the switch is driven to an OFF state, i.e. no conduction between the source and drain. On the other hand, when a positive voltage is applied to the gate, the switch is turned ON resulting in connection of the source to the drain. Each detector element of the detector array is constructed with a respective transistor and is controlled in a manner consistent with that described below.

Specifically, during exposure to x-rays, negative voltage is applied to all gate lines resulting in all the transistor switches being driven to or placed in an OFF state. As a result, any charge accumulated during exposure is stored in each detector element capacitor. During read out, positive voltage is sequentially applied to each gate line, one gate at a time. In this regard, only one detector element is read out at a time. A multiplexer may also be used to support read out of the detector elements in a raster fashion. An advantage of sequentially reading out each detector element individually is that the charge from one detector element does not pass through any other detector elements. The output of each detector element is then input to a digitizer that digitizes the acquired signals for subsequent image reconstruction on a per pixel basis. Each pixel of the reconstructed image corresponds to a single detector element of the detector array.

As described above, indirect detection, digital x-ray detectors utilize a layer of scintillating material, such as Cesium iodide (CsI), to convert incident radiation to visible light that is detected by light sensitive regions of individual detector elements of a detector array. Generally, the transistor controlled detector elements are supported on a thin substrate of glass. The substrate, which supports the detector elements as well as the scintillator layer, is supported by a panel support. The support panel is not only designed to support the detector components, but also isolates the electronics for controlling the detector from the detector components. The electronics is supported by the base of a cover assembly enclosing the internal components of the x-ray detector.

The internal components of an x-ray detector, e.g. scintillator layer, detector array, glass substrate, etc., are relatively sensitive components that may fracture when subjected to relatively high levels of strain, stress, and acceleration. As such, when an x-ray detector is dropped, the internal components may be become damaged and degrade detector performance. As a result, the x-ray detector will require repair or replacement—two potentially costly solutions.

For instance, a user may not appreciate the degree to which an x-ray detector is dropped when the x-ray detector is, in fact dropped. In this regard, the user, such as a member of a hospital staff, may place the x-ray detector into use notwithstanding the damage caused to the x-ray detector as a result of the drop. Placing the x-ray detector can result in significant delay in acquiring usable data from a subject as the damage to the internal components of the x-ray detector will not be made apparent until data is acquired and reconstructed.

Since repair and replacement can be a time-consuming, arduous, and complex task, if a diagnostician diagnosing an inoperable or malfunctioning x-ray detector had specific insight as to whether the x-ray detector has been dropped, the diagnostic process may be expedited. That is, using empirical data, the diagnostician may be able to target the diagnostic process on the premise that given gravitational loads on the x-ray detector result in given damage to the x-ray detector and its components. For instance, if a diagnostician knew that the x-ray detector was subjected to a drop that placed a 10 g load on the x-ray detector, the diagnostician may able to discern that more than likely the glass substrate has fractured without disassembling the detector.

Therefore, it would be desirable to have an x-ray detector that detects and provides an output of the gravitational forces placed thereon whereby the output may be readout electronically such that diagnosis may be carried out without disassembly of the detector. It would be further desirable to have an x-ray detector that time and date stamps the gravitational loads placed thereon and stores this historical data in such a manner that it can be accessed to determine with specificity when the gravitational forces were placed on the detector.

BRIEF DESCRIPTION OF THE INVENTION

The present invention is a directed to an x-ray detector that electronically detects and measures gravitational loads placed thereon that overcomes the aforementioned drawbacks.

A method and system of electronically detecting and measuring gravitational loads placed on an x-ray detector is disclosed. An x-ray detector incorporates an accelerometer that detects and provides an output as to the extent of gravitational loads or forces placed thereon. The accelerometer reading is also time and/or date stamped for each recorded event such that one may determine when the x-ray detector was subjected to a particular load. A microcontroller/microprocessor may also compare a current reading of the accelerometer to a threshold and, based on the comparison, provide an audio or visual indication that the x-ray detector has been subjected to a potentially damaging gravitational load.

Therefore, in accordance with one aspect, the present invention includes an x-ray imaging system having an x-ray detector configured to detect radiation emitted by an x-ray source and attenuated by a subject to be imaged. The x-ray detector is also configured to provide an electrical output that may be processed for reconstruction of an image of the subject. The x-ray imaging system further has an electronic sensor configured to detect gravitational loads placed on the x-ray detector.

In accordance with another aspect, the present invention includes an x-ray detector having a scintillator configured to emit light in response to reception of radiation and a detector element array having a plurality of detector elements each configured to detect light emissions from the scintillator and provide an electrical signal containing data that may be processed for image reconstruction. An accelerometer is provided and is configured to detect and measure gravitational loads placed on the x-ray detector.

According to another aspect, the present invention includes an x-ray scanner having an x-ray source configured to project radiation at a subject and an x-ray detector configured to detect radiation projected at and attenuated by the subject. The x-ray detector has an electronic means of measuring a gravitational load placed on the x-ray detector. The x-ray scanner further has a controller configured to read out data from the electronic means and determine if the x-ray detector has been subjected to a potentially damaging gravitational load.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention will be described with respect to a flat panel, solid-state, indirect detection, portable digital x-ray detector for use with a mobile x-ray imaging system. However, the present invention is equivalently applicable with other types of x-ray detectors including direct detection digital detectors. Additionally, the present invention may be used with stationary or fixed room x-ray imaging systems. Further, the present application makes reference to an imaging "subject" as well as an imaging "object". These terms are not mutually exclusive and, as such, use of the terms is interchangeable and is not intended to limit the scope of the appending claims.

Figure 1:
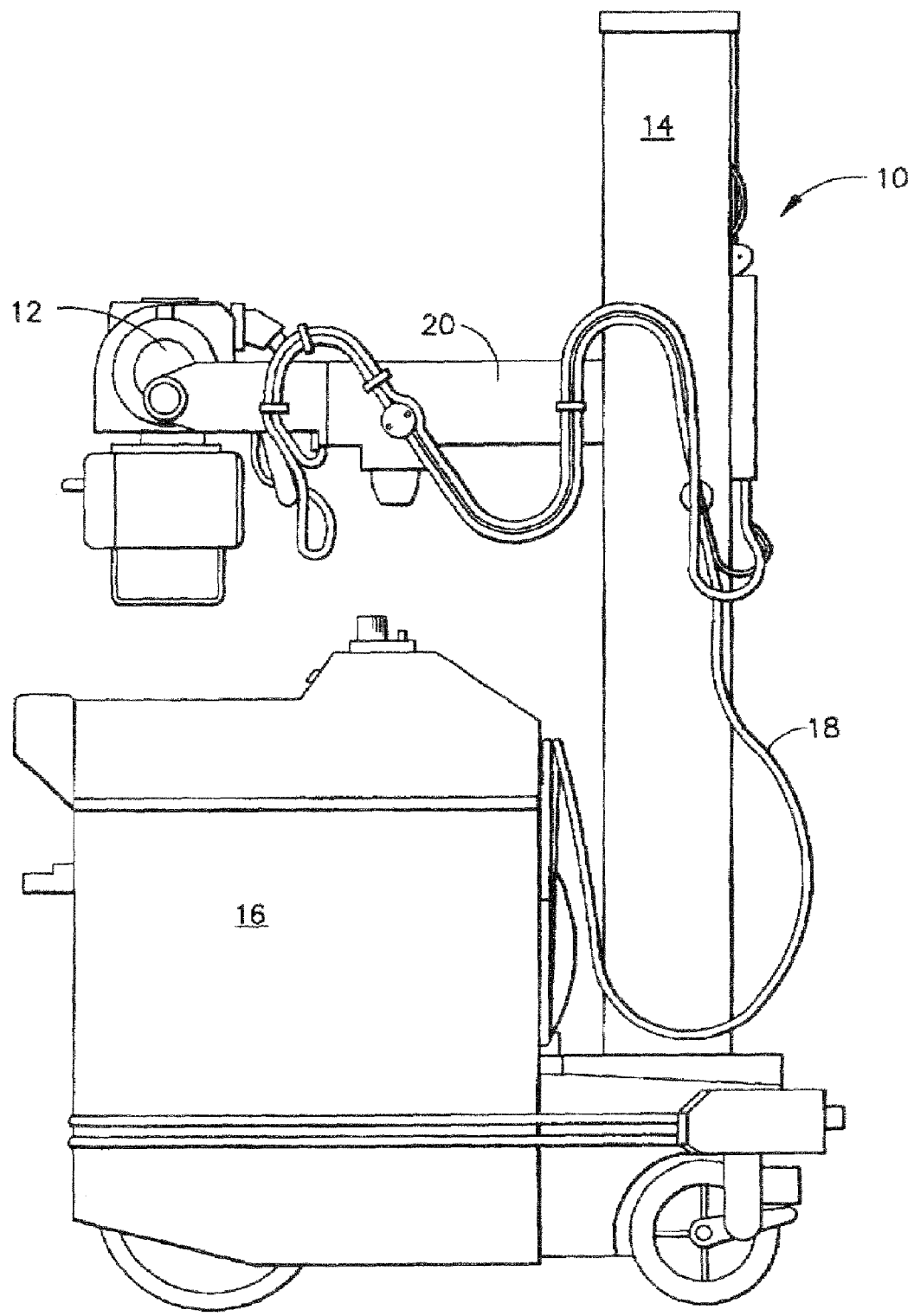
FIG. 1 is a pictorial view of an exemplary mobile x-ray imaging system.

Referring now to FIG. 1, an exemplary mobile x-ray imaging system 10 applicable with a portable x-ray detector incorporating the present invention is shown. An x-ray source 12 is mounted or otherwise secured to an end of horizontal arm 20. Arm 20 allows the x-ray source 12 to be variably positioned above a subject in such a manner so as to optimize irradiation of a particular area of interest. The x-ray source 12 is typically mounted through a gimbal-type arrangement (not shown) in column 14. In this regard, the x-ray source may be rotated vertically from a rest or park position on the mobile x-ray unit base 16 to the appropriate position above the subject in order to take an x-ray exposure of the subject. The rotational movement of column 14 is typically limited to a value of 360 degrees or less to prevent entanglement of high voltage cables 18 used to provide electrical power to the x-ray source 12. Cables 18 may be connected to a utility line source (not shown) or a battery (not shown) in the base 16 to energize the x-ray source 12 as well as other electronic components of the system 10. One skilled in the art will appreciate that system 10 may be equipped or connectable to a display unit (not shown) for the display of images captured from the imaging subject.

Figure 2:
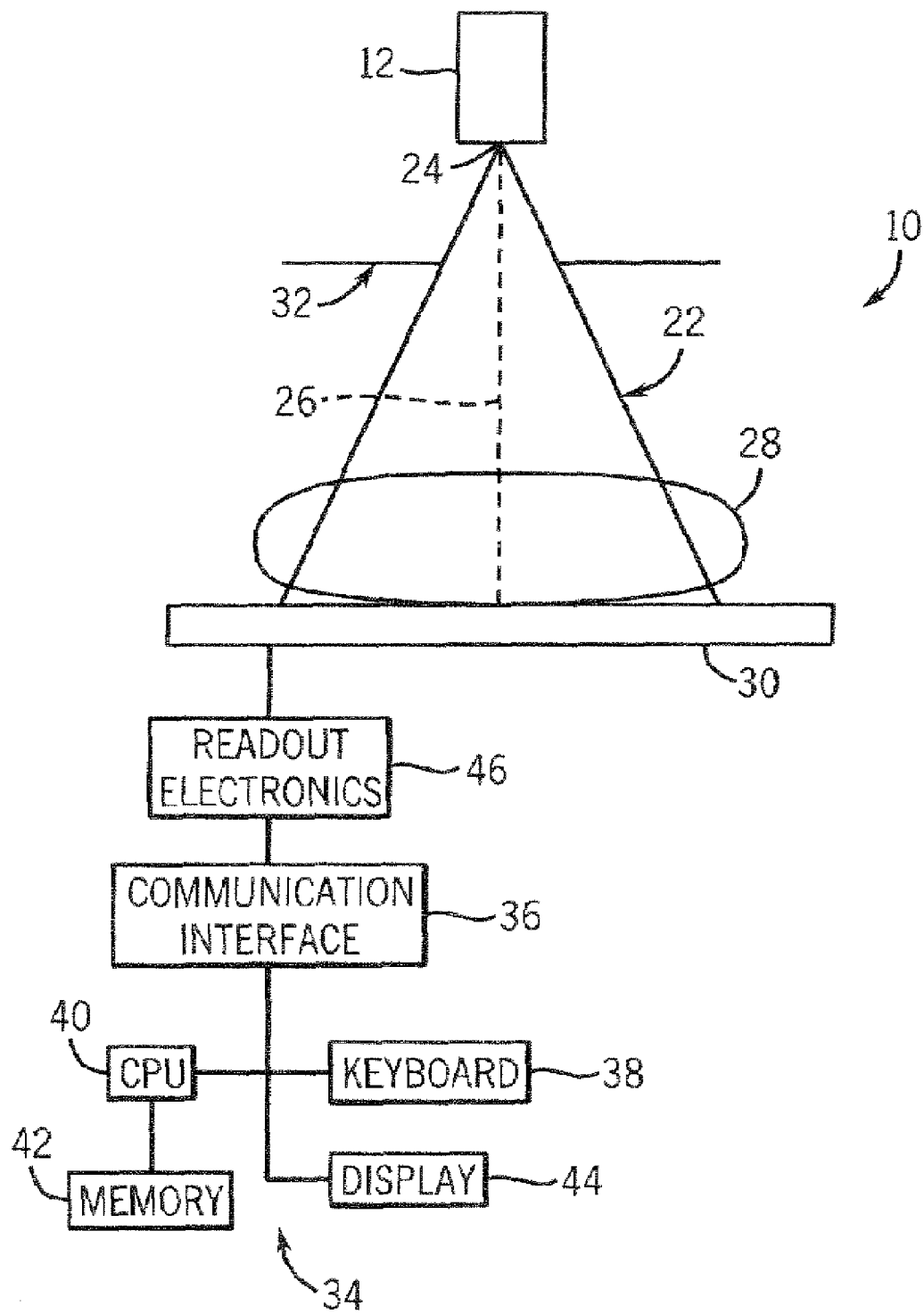
FIG. 2 is a schematic block diagram of the exemplary x-ray imaging system shown in FIG. 1.

Referring now to FIG. 2, a schematic of x-ray imaging system 10 is illustrated. As referenced above, system 10 includes x-ray source 12 designed to project a fan bean of irradiation 22 from focal spot 24 along axis 26 toward an object to be imaged 28. One skilled in the art will appreciate that medical patients as well as luggage, packages, and the like may be non-invasively inspected using the exemplary x-ray imaging system 10. A flat panel digital detector 30 detects x-rays passing through and attenuated by object 28. A collimator assembly 32, schematically shown in FIG. 2 as comprising collimator blades, may be used to collimate the x-ray fan beam 22 to control the scope of irradiation.

A host or scanner interface 34 includes a communication interface 36, a keyboard 38 or other data entry device, a CPU 40, memory 42, and a display unit 44, such a computer monitor, to display reconstructed images of the object. A bus 46 connects the keyboard 38, CPU 40, memory 42, and display unit 44 to the communication interface 36. The CPU may include a microprocessor, digital signal processor, microcontroller, as well as other devices designed to carry out logic and processing operations. Signals corresponding to an x-ray image are read out from flat panel detector 30 via readout electronics 46. While not shown, it is contemplated that the host interface 34 may be connected to a centralized facility via the Internet or communications link for monitoring and maintenance.

Additionally, the readout electronics may read out signals from the flat panel detector across a tethered connection between the detector and the imaging system. It is also contemplated that read out may be achieved across a wireless communication between the detector and imaging system. In this regard, one skilled in the art will appreciate that the imaging system and detector may be equipped with transceivers, antennas, and other operational circuitry to support the wireless transmission of data.

Figure 3:
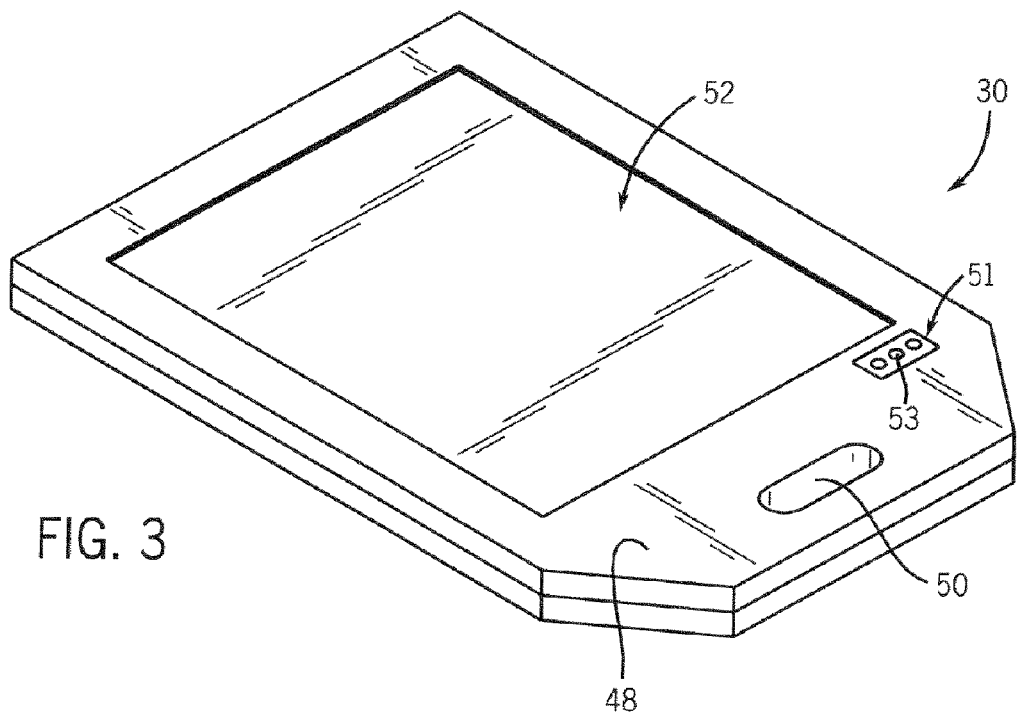
FIG. 3 is a perspective view of a portable, solid-state, flat panel, digital x-ray detector incorporating the present invention.

Referring now to FIG. 3, a perspective view illustrates a portable, flat panel x-ray detector 30 incorporating the present invention. Detector 30 is preferably an indirect detection, solid-state, digital detector that determines x-ray attenuation through an imaging subject from the emission of light by a scintillator that emits light upon the incidence of x-rays. The detector 30 includes a cover 48 formed of lightweight, durable composite material. A handle 50 is incorporated into the cover to support the portability of the detector. As shown, the detector 30 may be constructed without a fixed tether. In this regard, the detector may be connected to a tether (not shown), which is connected to the readout electronics when in use. When not in use, the detector may be easily detached from tether and stored remotely from the imaging system. The top of the cover includes a template 52 that visually defines the surface dimensions of the scintillator layer in the detector. Template 52 is designed to visually assist a user in positioning of the detector for data acquisition. The x-ray detector preferably includes an LED bank 51 that includes one or more LEDs 53 that may be illuminated to provide operational and/or diagnostic feedback.

While the present invention is particularly applicable with indirect detection digital detectors, the present invention may also be implemented with direct detection digital detectors. Direct detection digital detectors utilize a layer of amorphous selenium or a material of similar properties coupled to a thin film transistor array. X-ray interaction in the selenium layer releases electrons (or electron holes), which are used to form signal directly. An electrode is often used to create an electric field across the selenium layer to minimize the lateral spread of electrons, preserving spatial resolution. In addition to selenium, mercuric iodide, cadmium telluride, and lead iodide may be used.

Figure 4:
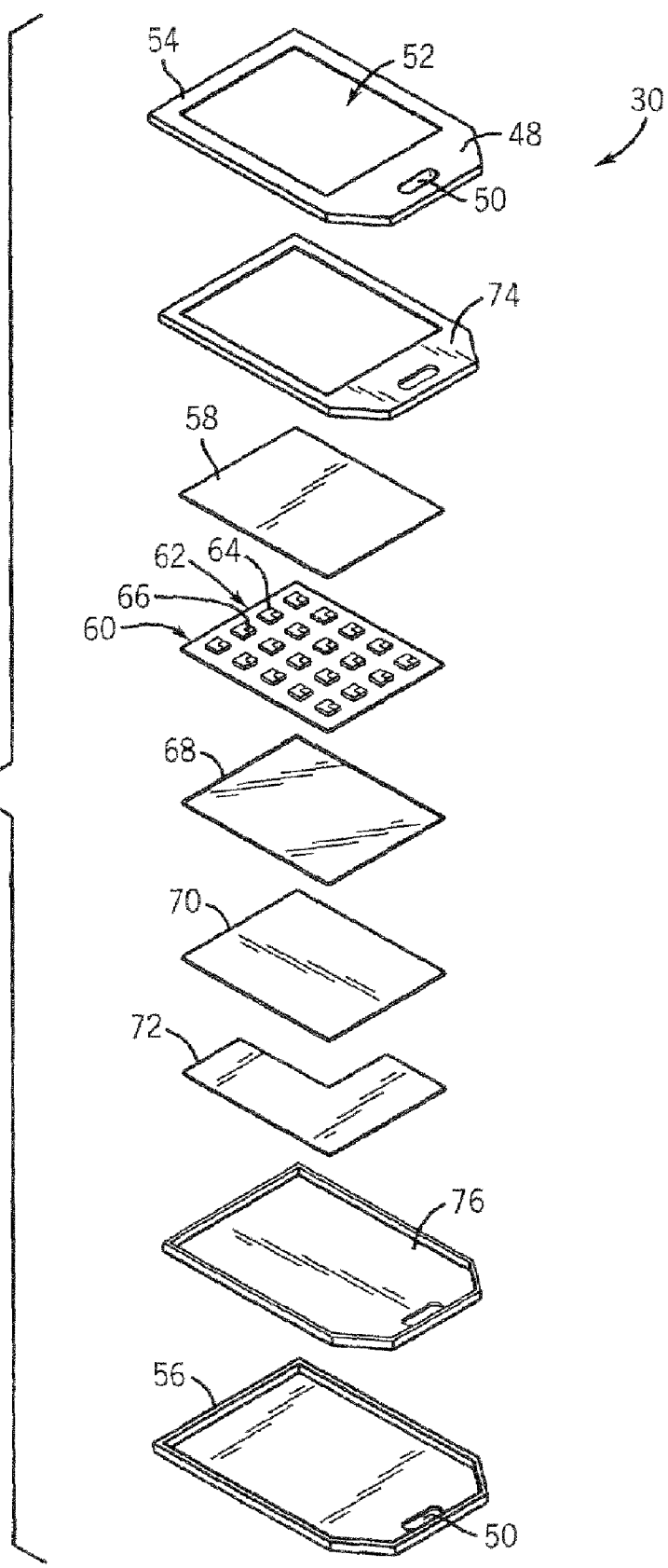
FIG. 4 is an exploded view of the x-ray detector shown in FIG. 3.

Referring now to FIG. 4, an exploded view schematically illustrates the internal composition of detector 30. Detector 30 includes a top cover 54 that along with base cover 56 provides a shell or enclosure for its internal components. Both covers 54, 56 are preferably formed of a composite material, such as carbon graphite, and impact-absorbing material, such as viscoelastic foam, so as to house and protect the detector components from fracture when exposed to a load or dropped. Covers 54 and 56 may be constructed with bumpers, foam inserts, layers of impact absorbing material, and the like to inhibit fracturing of the detector components when dropped or exposed to a load. When assembled, the top cover 54 is constructed in such a manner that the detector may be placed on a floor and support a standing subject. In this regard, the top cover panel 54 is designed to minimally deflect when subjected to a load.

Top cover 54 and base cover 56 collectively form handle 50 when assembled. The handle supports portability of the detector. Additionally, the detector is constructed to be quickly detached from a tether (not shown) that is used to connect the detector to the scanner during data acquisition and readout. That is, the detector may include a quick-connect connector or socket designed to receive a tether without requiring user access to an internal control panel of the detector. When un-tethered, detector 30 may be transported to and from multiple scan stations remote from one another. This is particularly advantageous for emergency rooms and other triage facilities. Further, the portability and detachability of the detector further enhances the mobility of a mobile x-ray imaging system, such as that shown in FIG. 1.

Detector 30 further includes a scintillator layer 58 designed to convert incident x-rays or gamma rays to visible light. Scintillator layer 58, which may be fabricated from CsI or other scintillating material, is designed to emit light proportional to the number and energy of the x-rays received. As such, light emissions will be higher in those regions of the scintillator layer 58 where either more x-rays were received or the energy level of the received x-rays was higher. Since the composition of the subject will attenuate the x-rays projected by the x-ray tube, the energy level of the x-rays impinging upon the scintillator layer will not be uniform across the scintillator layer. This variation in light emission will be used to capture contrast in the reconstructed image.

The light emitted by the scintillator layer 58 is detected by detector elements of a detector element array 60. Each detector element 62 corresponds to a picture element or pixel in the reconstructed image. Each detector element 62 includes a light sensitive or photoconductive region 64 and an electronics region 66. During exposure to x-rays, electrons are released in the light sensitive region 64 in proportion to the light detected in the region 64. The electronics region 66 includes a capacitor (not shown) that stores the electrical charge accumulated by the light sensitive region. After exposure, a thin-film-transistor (not shown) in the electronics region 66 is biased so as to connect the capacitor to readout electronics in the x-ray scanner. Generally, a multiplexer (not shown) is used to control read out of the discrete detector elements in a sequential, raster fashion. In this regard, the output of each detector element is sequentially input to a digitizer for digitization for subsequent image reconstruction.

The thin-film-transistors of the detector elements 62 are supported by a glass substrate 68. Lead lines (not shown) etched in substrate 68 are used for routing of the electrical output of the detector elements as well as applying the biasing voltages to the thin-film-transistors. The glass substrate is generally very thin and fragile. In this regard, as referenced above, the top cover and base cover 54 and 56 are designed with impact absorbing material to help prevent fracturing of the glass substrate. Additionally, as the detector 30 may be used to support a relatively large load during imaging, e.g. imaging of the feet of an average sized adult male, the top cover panel 54 is further designed to reduce the stress on the detector to further prevent fracturing of the glass substrate and other detector components.

The glass substrate 68 is supported by a detector panel support 70. Panel support 70 is not only designed to support substrate 68, but is also used to separate the x-ray conversion and light detection components from the electronics 72.

Panel support 70 is constructed to include radiation absorbing material in addition to structurally supporting material. Incorporating radiation absorbing material within the panel support reduces or eliminates the detection of backscattered x-rays. That is, the radiation absorbing material absorbs x-rays passing through the scintillator layer, detector element array, and glass substrate, as well as x-rays that deflect off the back cover of the detector. In this regard, the electronics 72 are not imaged.

Electronics 72, in one embodiment, have an L-shape and is disposed to support the processing and logic control electronics of the detector. The electronics preferably includes LEDs for monitoring operation and diagnostics of the detector. The electronics may also include temperature sensors for providing feedback as to the temperature of the detector as well as the temperature of the subject. As will be described, the electronics may also support one or more accelerometers or other gravitational force detectors designed to detect acceleration of the detector and store data accordingly. The accelerometer(s) may be sensitive to one or more dimensions, i.e. one, two, or three axes). In this regard, an accelerometer may be used to record the date and time when the detector experienced dramatic increases in acceleration, i.e. when dropped. The electronics may also include various storage devices including flash storage. In a wireless implementation, the electronics may include an antenna and transceiver for wirelessly transmitting data to the x-ray scanner. Additionally, the electronics may include a battery or other DC power source for powering the detector electronics. The electronics are supported by base cover panel 56.

As described above, the x-ray detector is designed to withstand relatively high-energy impacts, stresses, and strains such that the relatively sensitive components, i.e. scintillator layer, detector element array, glass substrate, and motherboard of electronics, are not damaged when the detector is dropped or stepped upon. In this regard, in one embodiment, the x-ray detector 30 includes two layers of impact-absorbing material 74, 76. One layer 74 is sealed against or otherwise placed in proximity to the undersurface of top cover panel 54 so as to be sandwiched between the top cover panel and scintillator layer 58. The other layer 76 is sealed or otherwise placed in proximity to the top surface of base panel 56 so as to be sandwiched between motherboard 72 and base panel 56. While two impact-absorbing layers 74, 76 are shown, it is contemplated that the detector may include only a single layer which is preferably sealed against the undersurface of top cover panel 54 or multiple layers interstitially disposed between the detector components. In this regard, the impact-absorbing material is designed not to attenuate radiation and, as such, does not interfere with data acquisition.

The impact-absorbing material is preferably a viscoelastic material that is designed to absorb the shock and vibrations placed on the detector when dropped but also deflect the force placed on the detector when stepped upon or otherwise subjected to a load, e.g. a standing patient for a foot/feet scan. In this regard, the impact absorbing material will deform when subjected to a load, but also recover its shape when the load is removed. As such, the impact-absorbing material has a memory.

The viscoelastic material, which may be foam or other plastic, is designed to deflect and absorb stresses and strains on the detector. As such, when the detector is stepped upon or dropped, the internal components of the detector, e.g. scintillator layer, detector element array, glass substrate, and motherboard, do not fracture or are otherwise damaged. One skilled in the art will appreciate that the thickness, density and composition of the impact-absorbing material may be variably selected to define the limits by which the detector may be subjected to a load or dropped without damage to the detector components. Preferably, however, the detector should have sufficient impact absorbing material such that the damage does not result when the detector is dropped a distance of 20 cm. and/or subjected to a point-load of 370 lbs.

Further, it is contemplated that layers 74 and 76 can have similar or dissimilar thicknesses, and be composed of similar or dissimilar impact absorbing material(s). For example, layer 74 may be designed to be more absorbent and deflective than layer 76. In this regard, layer 74 may be thicker than layer 76 or formed from material with improved absorption and deflective characteristics. Additionally, layer 74 may be formed of foam having pronounced viscoelastic properties whereas layer 76 is formed of a polycarbonate, PVC, or other material with less pronounced viscoelastic characteristics.

Figure 5:
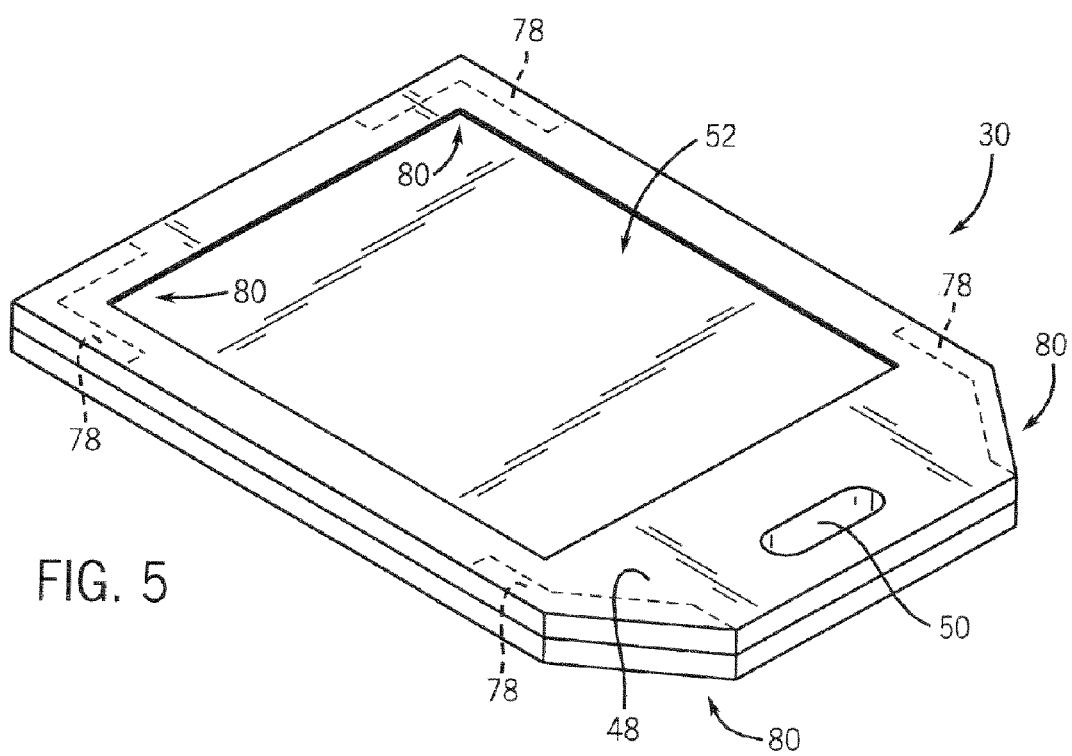
FIG. 5 is a perspective view of a portable, solid-state, flat panel, digital x-ray detector according to another embodiment of the present invention.

Referring now to FIG. 5, it is contemplated that the x-ray detector 30 may be constructed to have impact-absorbing inserts 78 placed in cavities positioned internally about the perimeter of the x-ray detector cover 48. The inserts may be positioned internally about the entire perimeter of the detector cover or, as illustrated in FIG. 5, positioned at identified impact zones 80. For example, inserts 78 may be positioned at each corner of the detector 30. Accordingly, when dropped, the detector is more likely to impact a floor or other surface at a corner. It is recognized that the detector may be constructed that its weight distribution increases the likelihood that that detector will impact the floor or other surface at a corner when dropped. By incorporating impact-absorbing material at the corners of the cover 48, the shock and resulting vibrations of the drop incident may be absorbed by the insert 78 and prevented from transferring to the internal components of the detector. It is recognized that the entirety of the shock may not be absorbed or otherwise deflected, but a sufficient percentage of the shock is absorbed such that any shock or vibration experienced by the internal components is of a magnitude insufficient to cause damage to the internal components. Additionally, by incorporating the inserts internally within the detector, the overall size and weight of the detector is negligibly increased, if any.

It is contemplated that the inserts 78 may be used in conjunction with a layer of impact-absorbing material positioned between the top cover and base panels and the internal components of the detector, such as that shown and described with respect to FIG. 4. In this regard, the layers of impact-absorbing material may be fabricated from materials with better deflective properties than impact absorption properties. On the other hand, the inserts 78 may be fabricated from materials having better impact absorption properties than deflective properties. As a result of this construction, the detector is able to handle greater point loads and greater impacts than that achieved with inserts or layers of impact absorbing material alone.

Figure 6:
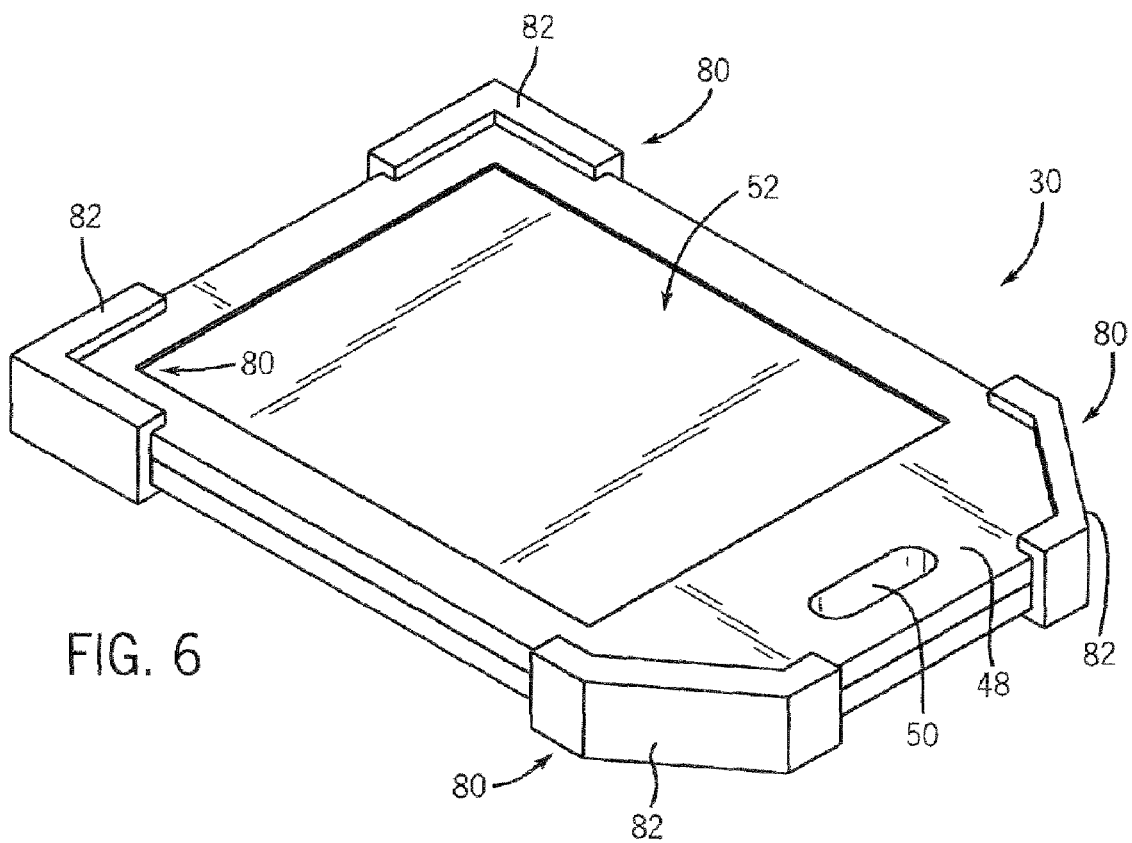
FIG. 6 is a perspective view of a portable, solid-state, flat panel, digital x-ray detector according to yet another embodiment of the present invention.

It is also contemplated that "bumpers" of impact-absorbing material may be secured, sealed, or otherwise connected to the external perimeter of the x-ray detector cover. This embodiment is illustrated in FIG. 6. As shown, bumpers 82 of impact absorbing material may be sealed against one or more corners of the detector cover 48. As the corners are identified as impact zones, the bumpers are shown at each corner. It is recognized that other impact zones may be identified around the perimeter of the cover 48 and, as such, receive a bumper. In this regard, it is contemplated that a continuous bumper may be sealed against the entire perimeter of the cover 48. In contrast to the embodiments described with respect to FIGS. 4 and 5, the bumpers 82 shown in FIG. 6 may increase the size of the detector. On the other hand, it is contemplated that the corners of the cover 48 may be replaced with bumpers 82 so as to not increase the size of the detector.

For instance, the cover 48 may be molded in such a manner that impact-absorbing material is used at the corners rather than the composite material used throughout the remainder of the cover. Or, cover 48 may be initially constructed without corners whereupon properly shaped wedges of impact-absorbing material may be glued or otherwise sealed to the cover so as to fill in the voids defined at the corners. Further, similar to the embodiment illustrated in FIG. 5, the detector of FIG. 6 may be constructed to include impact-absorbing material at selected impact zones as well as layers of impact-absorbing material such as that shown in FIG. 4.

Figure 7:
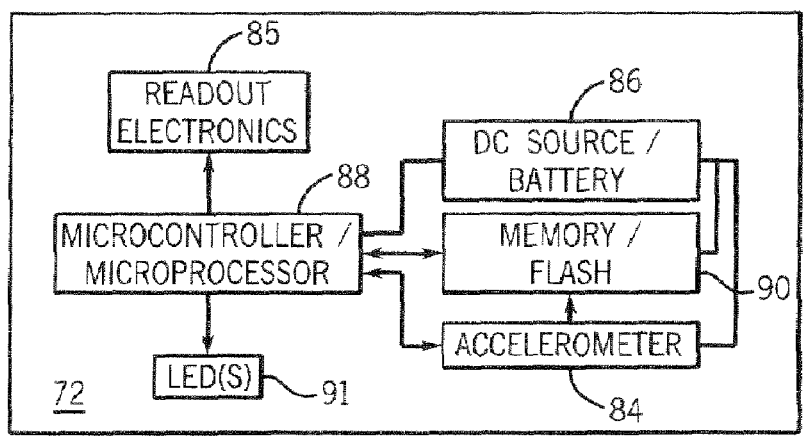
FIG. 7 is a schematic diagram of a portion of an x-ray detector control board according to the present invention.

Notwithstanding the damage prevention achieved by the x-ray detector described above, damage can result to an x-ray detector when dropped. While foam or other materials may be incorporated to soften the impact, the forces placed on the x-ray detector when dropped from a sufficient height may be sufficient to cause damage to the internal components of the detector, i.e. fracturing of the glass substrate. In this regard, and referring to FIG. 7, the x-ray detector includes an accelerometer 84 disposed on the control or circuit board of electronics 72. Once skilled in the art will readily appreciate that the control board of electronics includes readout electronics 85 as well as other components in addition to those illustrated. While it is preferred that an accelerometer be mounted on the control board 72, one skilled in the art will appreciate that an accelerometer may be mounted to other components of the x-ray detector, including, but not limited to an external surface of the top or base covers, the panel itself, or other subcomponents.

Accelerometer 84 is constructed to detect and measure gravitational loads placed on the x-ray detector. In short, an accelerometer detects when the x-ray detector is being dropped and measures the gravitational load placed on the x-ray detector during this gravitational event. The accelerometer is preferably a bi-axial detector and is designed to measure gravitational loads relative to two axes, i.e. the x and z axes or the y and z axes. One skilled in the art will appreciate, however, that the accelerometer may also be a tri-axial detector and, as such, measure gravitational loads relative to the x, y, and z axes. In an alternate embodiment, it may be advantageous to mount multiple accelerometers in multiple orientations to be able to cover multiple axes and/or be able to record forces on different components within the detector.

The accelerometer may be powered by a DC source 86, such as a battery, or powered in a conventional manner when the x-ray detector is tethered to the x-ray scanner. In this embodiment, the accelerometer only detects gravitational loads when the detector is connected to the scanner. In the embodiment implementing a DC source, however, accelerometer may detect and measure gravitational loads when the x-ray detector is disconnected from the x-ray scanner.

The accelerometer 84 may include a built-in microcontroller or controlled by the microcontroller/microprocessor 88 of the x-ray detector. The accelerometer 84 is designed to detect and measure gravitational loads at prescribed intervals, e.g. every 250 µsec. The microcontroller 88 then reads out data from the accelerometer 84 and, as will be described, processes the accelerometer output to determine if the x-ray detector is being or has been subjected to a damaging gravitational load. Either directly or via microcontroller 88, accelerometer 84 is connected to volatile memory 90, e.g. RAM or nonvolatile memory, e.g. FLASH, for storage of data associated with measured gravitational events. The RAM may be sized to store data for a single measured gravitational event or multiple measured gravitational events, e.g. nine measured gravitational events. As will be described, the accelerometer and/or microcontroller are designed to time and/or date stamp each measured and stored gravitational event. As a result, a diagnostician can ascertain when the x-ray detector was dropped and interpolate how far based on the measured gravitational load. As will be described, the microcontroller also is designed to illuminate one or more LEDs 91 based on the output of the accelerometer 84.

Figure 8:
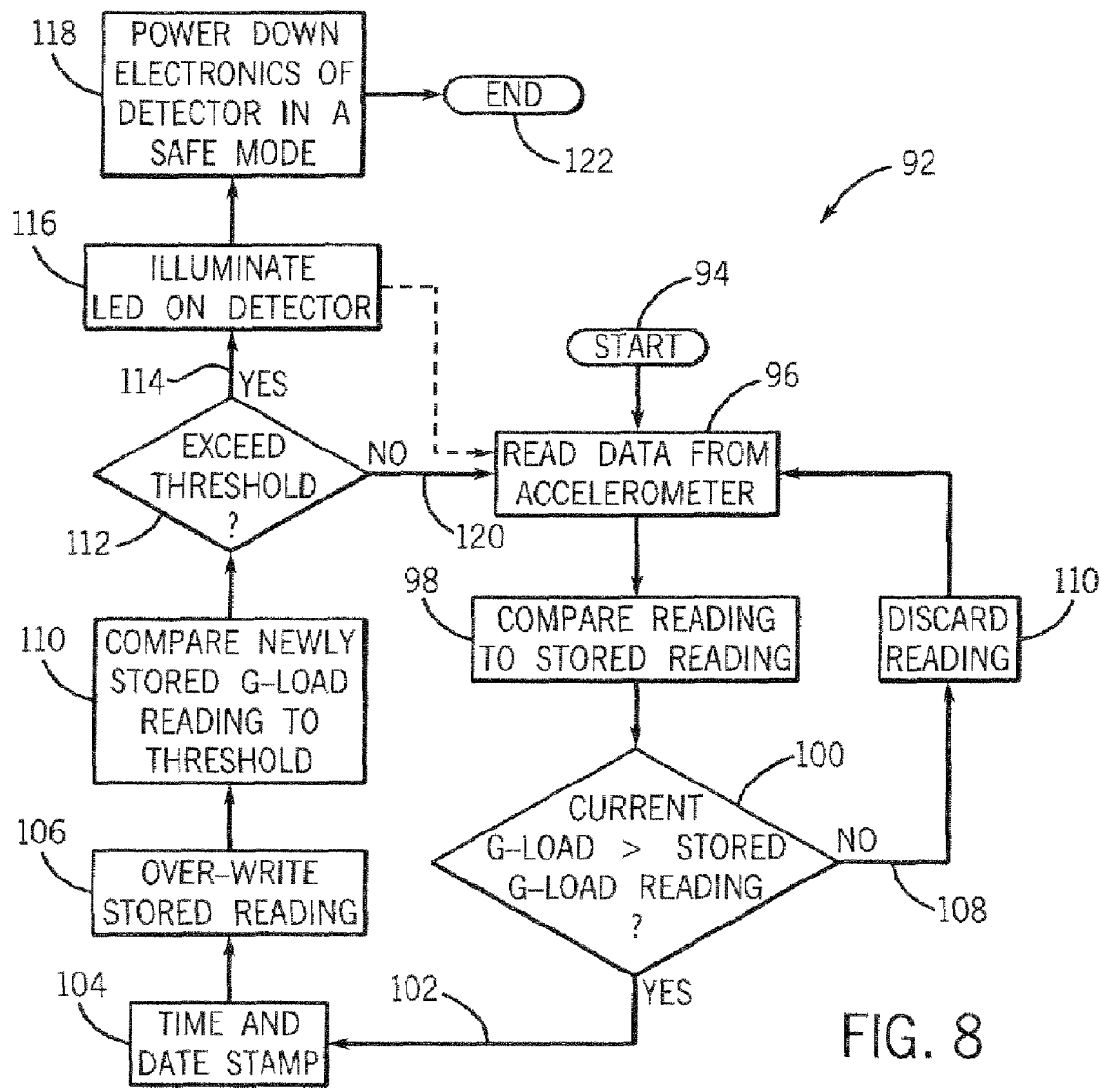
FIG. 8 is a flow chart setting forth the steps of a gravitational force monitoring and feedback technique according to the present invention.

Referring now to FIG. 8, the microcontroller is programmed to carry out a set of instructions that when executed cause the microcontroller to determine if the x-ray detector has been subjected to a potentially damaging gravitational load. This process 92 begins at 94 with powering up of the accelerometer or other electronic device capable of measuring gravitational forces. As referenced above, the accelerometer may be powered by a battery in the x-ray detector or powered by the x-ray scanner when the detector is tethered to the x-ray scanner. Once powered, the accelerometer, at prescribed intervals, samples the gravitational forces being placed on the x-ray detector. In one preferred embodiment, the accelerometer has a sampling rate of 4 kHz. Corresponding thereto, the controller reads out data from the accelerometer at 96. The accelerometer is configured to detect as well as measure the gravitational loads placed on the x-ray detector. The controller then compares the measured gravitational force of the measured gravitational event to that stored in a database log.

The present invention contemplates that a database or log of recorded events may be stored in memory, such as FLASH, in the x-ray detector. The log may be designed to maintain storage of multiple events or maintain a record of only one event. In any event, it is preferred that that log be sized to maintain a relatively limited number of records such that only a record of the larger gravitational load events is maintained and memory requirements are minimal. For instance, the log may be sized to maintain a record of ten gravitational events. It is preferred that the ten gravitational events corresponding to the ten largest gravitational loads be recorded.

Accordingly, the controller is caused to compare the magnitude of a current gravitational load to that stored in the log or database 100. If the magnitude of the current reading exceeds the magnitude of a stored or recorded event 100, 102, then the current reading is assigned a date and/or time stamp 104 and recorded in memory and the record corresponding to the lowest recorded magnitude is deleted or overwritten 106. On the other hand, if the magnitude of the current reading is less than the lowest recorded magnitude 100, 108, the current reading is discarded 110 and the controller continues to read data from accelerometer at 96.

If the log is designed to maintain a record of a single gravitational event then the process described above will be repeated while the accelerometer is powered such that the gravitational event measured to have the greatest gravitational load on the x-ray detector is recorded. It is also contemplated that the log may be reset when data is read out by a computer interface connected to the x-ray detector, such as the x-ray scanner. That is, the controller may clear out the log after data stored in the log is accessed.

It is also contemplated that the microcontroller may also compare the magnitude of the gravitational load of each recorded event to a threshold 110. As such, if the magnitude of the gravitational load of a recorded event exceeds a threshold 112, 114, an LED on the x-ray detector may be illuminated 116. Alternately, an audio warning may be sounded indicating that the x-ray detector may have been damaged when dropped thereby signaling to a user that the detector should not be used until examined. Both of which can be particularly advantageous for emergency room and other triage facilities where time is of the essence and the circumstances may not support the re-acquisition of data if the x-ray detector is damaged and not realized until after image reconstruction. It is also disclosed that the microcontroller can cause a "power-down" of the x-ray detector electronics into a "safe-mode" if a gravitational load in excess of the threshold is detected 118. In this "safe-mode" the x-ray detector may proactively issue an error condition to another subsystem or system. In this mode, the detector may not be operable for data acquisition and a corresponding output could be provided to the x-ray scanner indicating that the x-ray detector needs to be examined before used. After examined, the microcontroller can then "power-up" the electronics when an "all-clear" input is received. In addition, the safe mode may trigger a set of self-diagnostics to verify the status/state of the x-ray detector following the gravitational event.

If the threshold is not exceeded 112, 120, the process loops back to step 96 with continued readout of the accelerometer. The process terminates at 122 when the x-ray detector is disconnected from its power source. It is contemplated that for a battery-powered embodiment, the microcontroller may cause an audio and/or visual warning when battery power is low. As such, an operator may quickly replace the drained batteries to avoid lapses in monitoring of the gravitational loads to which the x-ray detector is exposed.

It is further contemplated that multiple thresholds may be used to segment out potential stresses to the x-ray detector. For instance, a cautionary warning may be provided if a gravitational load of intermediate magnitude is detected. On the other hand, a terminate-use warning may also be provided if the gravitational load is of a greater magnitude. These warnings may be provided via yellow and red illumination of LEDs on the x-ray scanner, respectively. Additionally, when connected to the x-ray scanner, a warning signal may be transmitted to the x-ray scanner and processed thereat such that an error message is displayed on a user interface.

Figure 9:
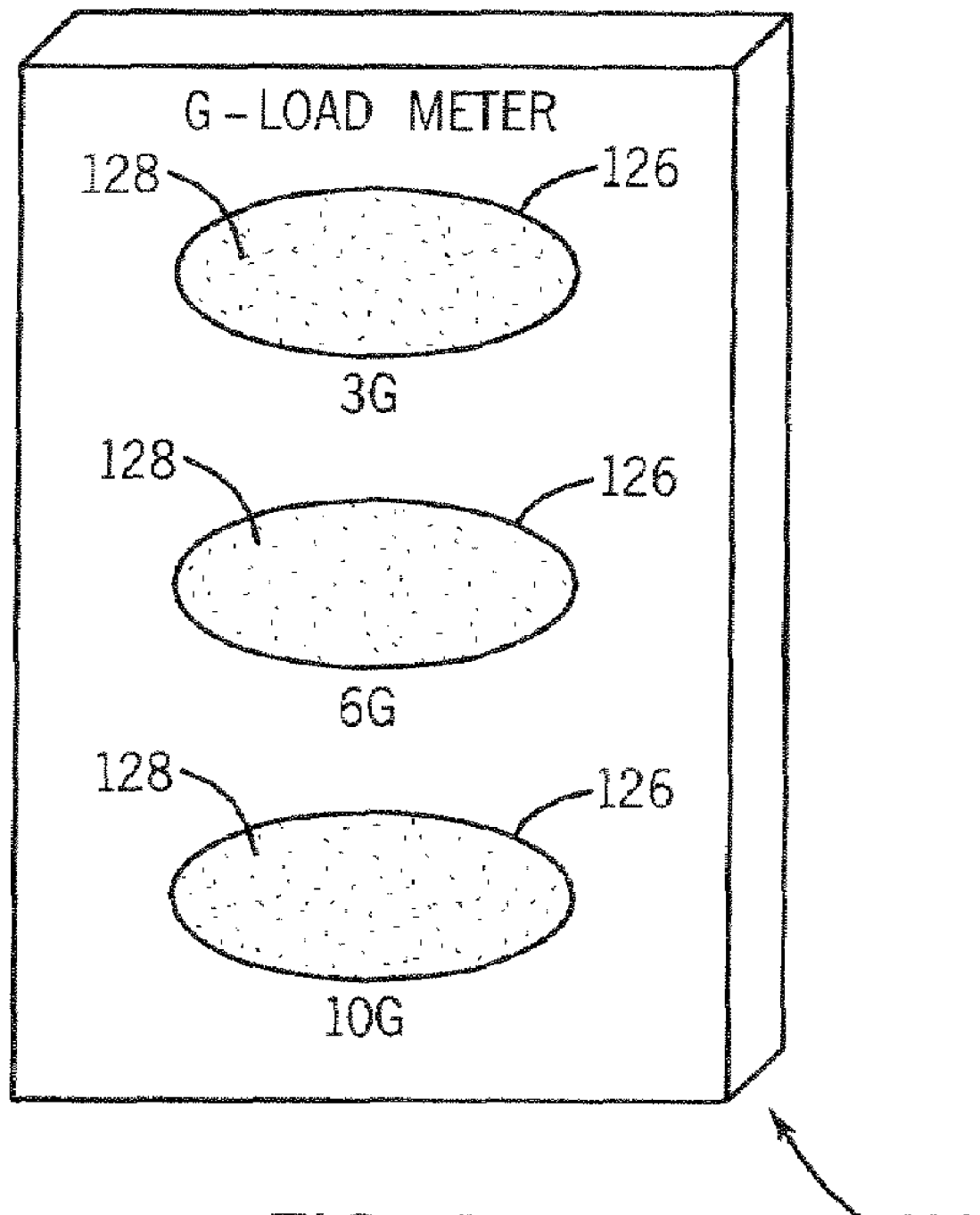
FIG. 9 is an elevated view of a mechanical gravitational load detector.

The x-ray detector may also be equipped with mechanical gravitational load detectors such as that illustrated in FIG. 9. This mechanical design 124 is conventional and includes multiple vials 126 of fluid 128. The fluid in each vial is designed to change color when subjected to a shock of sufficient strength. That is, when the fluid is "jarred" sufficiently, a chemical reaction is caused in each vile that results in a color change of the fluid. The composition of fluid in each vile can be set such that the chemical change does not occur until a specific gravitational load is experienced. For example, one vial may have a fluid therein that does not change color until a shock of 3 gs is experienced. As such, when the x-ray detector is subjected to a 3 g load, the fluid will change color. A drawback of such a mechanical design is that no distinction is made between a 4 g shock and a 10 g shock. At either magnitude, the fluid will change color. As such, it is preferred to use multiple vials, as illustrated, with each having fluid that changes color at different gravitational loads. In this regard, the mechanical detector provides a range of discrete measurements. For instance, a 4 g load will cause the fluid in a 3 g vial to change color but not change the fluid in a 6 g vial. Despite the advantages achieved with multiple vials, the mechanical design is limited in that a date or time is not associated with detected gravitational events. As such, it is preferred that an electronic sensor, such as an accelerometer, be used as a minimum. It is contemplated however, that a combination of electronic and mechanical detectors may also be implemented. This may be particularly advantageous for battery-less detectors. The mechanical sensors provide limited feedback for those drops that occur when the accelerometer in the x-ray detector is not powered.

A method and system of electronically detecting and measuring gravitational loads placed on an x-ray detector has been disclosed. The x-ray detector incorporates an accelerometer that detects and provides an output as to the extent of gravitational loads or forces placed thereon. The accelerometer or the x-ray detector microprocessor may also time and/or date stamp each recorded event such that a technician may determine when the x-ray detector was subjected to a particular load. A microcontroller/microprocessor may also compare a current reading of the accelerometer to a threshold and, based on the comparison, provide an audio or visual indication that the x-ray detector has been subjected to a potentially damaging gravitational load. As such, by having data available immediately after a drop, a user, such as a health care provider, can decide an appropriate action to take with respect to the x-ray detector after the gravitational event. For example, if the impact from a drop is slight, perhaps no action is required, if the impact was of medium impact, a customer-executable diagnostic test may be warranted, and finally if the stress was high, the user may be instructed to contact a repair technician for servicing of the x-ray detector.

Therefore, the present invention includes an x-ray imaging system having an x-ray detector configured to detect radiation emitted by an x-ray source and attenuated by a subject to be imaged. The x-ray detector is also configured to provide an electrical output that may be processed for reconstruction of an image of the subject. The x-ray imaging system further has an electronic sensor configured to detect gravitational loads placed on the x-ray detector.

The present invention also includes an x-ray detector having a scintillator configured to emit light in response to reception of radiation and a detector element array having a plurality of detector elements each configured to detect light emissions from the scintillator and provide an electrical signal containing data that may be processed for image reconstruction. An accelerometer is provided and is configured to detect and measure gravitational loads placed on the x-ray detector.

The present invention further includes an x-ray scanner having an x-ray source configured to project radiation at a subject and an x-ray detector configured to detect radiation projected at and attenuated by the subject. The x-ray detector has an electronic means of measuring a gravitational load placed on the x-ray detector. The x-ray scanner further has a controller configured to read out data from the electronic means and determine if the x-ray detector has been subjected to a potentially damaging gravitational load.

The present invention has been described in terms of the preferred embodiment, and it is recognized that equivalents, alternatives, and modifications, aside from those expressly stated, are possible and within the scope of the appending claims.

What is claimed is:

1. An x-ray imaging system comprising:
an x-ray detector configured to detect radiation emitted by an x-ray source and attenuated by a subject to be imaged, and provide an electrical output that may be processed for reconstruction of an image of the subject;
at least one electronic sensor configured to detect gravitational loads placed on the x-ray detector;
a controller configured to read out data from the at least one electronic sensor at predefined intervals and compare the gravitational load of a current reading of an electronic sensor to a threshold and illuminate an LED on the x-ray detector based on the comparison.

2. The system of claim 1 wherein the x-ray detector includes a circuit board with electronics to control operation of the detector and wherein the at least one electronic sensor is disposed on the circuit board.

3. The system of claim 1 wherein the at least one electronic sensor is powered by a power supply of an x-ray scanner when the x-ray detector is tethered to the x-ray scanner.

4. The system of claim 1 further comprising a battery disposed in the x-ray detector that provides power to the at least one electronic sensor.

5. The system of claim 1 wherein the controller is configured to read out data from the electronic sensor at 250 µs intervals.

6. The system of claim 1 wherein the controller is further configured to assign at least one of a time and a date stamp to each reading of an electronic sensor.

7. The system of claim 6 wherein the controller is further configured to store readings from an electronic sensor in a log.

8. The system of claim 7 wherein the controller is further configured to write over readings stored on the log such that a limited number of readings are stored in the log.

9. The system of claim 8 wherein the controller is further configured to compare the gravitational load from a current reading of an electronic sensor to that of a stored reading in the log and if the gravitational load of the current reading exceeds that of the stored reading, then overwrite the stored reading with the current reading.

10. The system of claim 1 wherein the controller is further configured to illuminate a failure LED if the gravitational load of a current reading of an electronic sensor is equal to or greater than a maximum allowable gravitational load.

11. The system of claim 1 wherein the controller is further configured to power down electronics of the x-ray detector if the gravitational load of a current reading of an electronic sensor is equal to or greater than a maximum allowable gravitational load.

12. The system of claim 1 wherein the controller is further configured to provide an error message to a processor to be used to warn a user of a potentially damaging gravitational event.

13. The system of claim 1 wherein the controller is further configured to proactively initiate and report self-test diagnostics in response to a threshold exceeding gravitational event.

14. The system of claim 1 wherein the threshold is 10 G.

15. The system of claim 1 wherein the x-ray detector includes flash storage connected to store data output by the electronic sensor.

16. The system of claim 1 further comprising one or more mechanical sensors that mechanically detect gravitational loads placed on the x-ray detector.

17. The system of claim 16 wherein the one or more mechanical sensors includes a fluid filled label sealed to a surface of the x-ray detector, wherein the fluid changes color when exposed to a given gravitational load.

18. The system of claim 1 wherein the at least one electronic sensor includes a plurality of accelerometers.

19. An x-ray imaging system comprising:
an x-ray detector configured to detect radiation emitted by an x-ray source and attenuated by a subject to be imaged, and provide an electrical output that may be processed for reconstruction of an image of the subject;
at least one electronic sensor configured to detect gravitational loads placed on the x-ray detector; and
one or more mechanical sensors that mechanically detect gravitational loads placed on the x-ray detector, wherein the one or more mechanical sensor includes a fluid filled label sealed to a surface of the x-ray detector, wherein the fluid changes color when exposed to a given gravitational load.

* * * * *